United States Patent
Chiou et al.

(10) Patent No.: US 9,872,912 B2
(45) Date of Patent: Jan. 23, 2018

(54) METHOD FOR TREATING PANCREATIC CANCER

(71) Applicant: CHINA MEDICAL UNIVERSITY, Taichung (TW)

(72) Inventors: Tzyy-Wen Chiou, Taichung (TW); Horng-Jyh Harn, Taichung (TW); Shinn-Zong Lin, Taichung (TW); Yi-Wen Chou, Taichung (TW); Mao-Hsuan Huang, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 14/520,050

(22) Filed: Oct. 21, 2014

(65) Prior Publication Data
US 2015/0352213 A1 Dec. 10, 2015

(30) Foreign Application Priority Data
Jun. 4, 2014 (TW) .............................. 103119393 A

(51) Int. Cl.
| A61K 47/34 | (2017.01) |
| A61K 31/365 | (2006.01) |
| A61K 9/00 | (2006.01) |
| A61K 31/343 | (2006.01) |

(52) U.S. Cl.
CPC .............. *A61K 47/34* (2013.01); *A61K 9/00* (2013.01); *A61K 31/343* (2013.01); *A61K 31/365* (2013.01)

(58) Field of Classification Search
USPC ........................................................ 514/470
See application file for complete search history.

(56) References Cited

U.S. PATENT DOCUMENTS

| 8,247,444 B2 * | 8/2012 | Chen .................... A61K 31/365 514/462 |
| 2007/0134351 A1 | 6/2007 | Luo et al. |
| 2010/0158798 A1 | 6/2010 | Skordalakes |
| 2012/0121587 A1 | 5/2012 | Maeda et al. |

FOREIGN PATENT DOCUMENTS

| CN | 1943606 | 4/2007 |
| CN | 101264271 A | 9/2008 |
| CN | 101835899 | 9/2010 |
| CN | 102641477 A | 8/2012 |
| EP | 2 343 051 * | 7/2011 |
| EP | 2 343 051 A2 | 7/2011 |
| TW | 200616656 | 6/2007 |
| TW | 201106947 | 3/2011 |
| WO | 2010/131733 | 11/2010 |

OTHER PUBLICATIONS

Ham, et al., Neuro-Oncology 13(6):635-648, 2011.*
Kelly et al., Histopathology Primary hepatocellular carcinoma of the pancreas: a case report and review of the heterogeneous group of pancreatic hepatoid carcinomas. First published: Feb. 9, 2012 vol. 60, Issue 6, May 2012, pp. 1012-1015.*
Sigurdsson, et al., Anticancer Research 25:1877-1880 (2005).*
Holisticonline Herbal-med at Http://holisticonline.com/herbal-med/_herbs/h4.htm, 2000.*
Herb Society of America Fact sheet, http://www.herbsociety.org/factsheets/angelica.pdf, 2005.*
Domb et al., Handbook of Biodegradable Polymers, 1997, ISBN 90-5702-153-6.*
Domb and Langer, Journal of Polymer Science: Part A: Polymer Chemistry, vol. 25, 3373-3386 (1987).*
Meschino, J. A Comprehensive Guide to Angelica Species, http://www.meschinohealth.com/books/angelica species, 2012.*
Fernandez, et al., Cancer, Epidemiology, Biomarkers and Prevention, vol. 3, 209-212, Apr./May 1994.*
Domb, A. J. et al., "Polyanhydrides. I. Preparation of high molecular weight polyanhydrides", Journal of Polymer Science Part A: Polymer Chemistry, vol. 25, Issue 12, pp. 3373-3386, Dec. 1987.
Walter, K. A. et al., "Interstitial taxol delivered from a biodegradable polymer implant against experimental malignant glioma", Cancer Research, vol. 54(8), pp. 2207-2212, Apr. 1994.
Weingart, J. D. et al., "Local delivery of the topoisomerase I inhibitor camptothecin sodium prolongs survival in the rat intracranial 9L gliosarcoma model", Int. J. Cancer. vol. 62(5), pp. 605-609, Sep. 1995.
Yuan, P. et al., "Virtual Evaluation on the Activities of Phthalides and Terpenoids from Angelica sinensis," Chinese Herbal Medicines, 2010, vol. 2(3), pp. 236-241.

* cited by examiner

*Primary Examiner* — Kathrien Cruz
(74) *Attorney, Agent, or Firm* — Ping Wang; Andrews Kurth Kenyon LLP

(57) ABSTRACT

A method for treating pancreatic cancer is provided. The method comprises administering to a subject in need thereof a therapeutically effective amount of a pharmaceutical formulation, wherein the pharmaceutical formulation comprises (Z)-butylidenephthalide and is substantially free of (E)-butylidenephthalide.

18 Claims, 10 Drawing Sheets
(8 of 10 Drawing Sheet(s) Filed in Color)

METHOD FOR TREATING PANCREATIC CANCER

CROSS-REFERENCES TO RELATED APPLICATIONS

Not applicable.

BACKGROUND OF THE INVENTION

Field of the Invention

The present invention relates to the uses of a pharmaceutical formulation, which comprises (Z)-butylidenephthalide, especially to the uses of the pharmaceutical formulation in treating pancreatic cancer.

Descriptions of the Related Art

The pancreas is a soft, elongated gland located in the back of the abdominal cavity of a living body. In general, the pancreas of a human has a length ranging from about 15 cm to 20 cm, a width of about 2.5 cm, and a weight ranging from about 75 grams to 100 grams. "Pancreatic cancer" refers to a malignant tumor that is generated from pancreatic cells. Ductal adenocarcinomas accounts for 90% of pancreatic cancers, wherein about 80% occurs within the head of the pancreas gland.

Pancreatic cancer tends to occur in the elderly, and the incidence rate in males is twice as high as that in females. Early pancreatic cancer usually does not show obvious symptoms, but along with the gradual growth of pancreatic tumors, patients may show symptoms of abdominal pain, back pain, jaundice, weight loss, and diarrhea. In addition, typical pancreatic cancer appears fibrosis and adhesion to surrounding tissue. Because pancreatic cancer cells often penetrate into peripheral nerves and/or invade blood vessels, almost 90% of pancreatic cancer is not treatable through surgery. Pancreatic cancer has a poor prognosis, and the five-year survival rate is less than 5%.

Current clinical therapy for pancreatic cancer includes surgery, chemotherapy and irradiation therapy, etc. In general, when the condition of a patient of pancreatic cancer allows, surgery is the first line treatment in increasing the survival rate. As for the chemotherapy, a single medicament, such as the anti-metabolites medicaments of 5-fluorouracil (5-FU) and gemcitabine, or a combination of various medicaments can be chosen based on the clinical stage of pancreatic cancer. However, the therapeutic efficacy of chemotherapy is low. Traditional chemotherapy is almost ineffective in the case of pancreatic cancer recurrence. Irradiation therapy is usually used as an adjuvant therapy during the treatment for pancreatic cancer because this therapy cannot cure unresectable pancreatic tumor. Therefore, there is still a need for a medicament for treating pancreatic cancer.

The inventors of the present invention found that Z-butylidenephthalide (Z-BP) can inhibit the growth of pancreatic cancer cells, and thus, can be used to treat pancreatic cancer. In particular, a controlled release dosage form containing Z-butylidenephthalide can be implanted into the area with pancreatic cancer cells after surgery, to achieve a locally stable high dose of Z-butylidenephthalide. As a result, Z-butylidenephthalide can penetrate into surrounding pancreatic tissue to kill "invasive residual cancer cells," to achieve the desired therapeutic effect.

SUMMARY OF THE INVENTION

An objective of the present invention is to provide a pharmaceutical formulation for treating pancreatic cancer, wherein the pharmaceutical formulation comprises (Z)-butylidenephthalide, and is substantially free of (E)-butylidenephthalide. Preferably, in the pharmaceutical formulation, (Z)-butylidenephthalide is included in a biocompatible polymer matrix pharmaceutical formulation in a controlled release dosage form.

Another objective of the present invention is to provide the use of a pharmaceutical formulation in the manufacture of a medicament, wherein the medicament is used for treating pancreatic cancer. The pharmaceutical formulation comprises (Z)-butylidenephthalide, and is substantially free of (E)-butylidenephthalide. Preferably, in the pharmaceutical formulation, (Z)-butylidenephthalide is included in a biocompatible polymer matrix, to provide a medicament in a controlled release dosage form.

Yet another objective of the present invention is to provide a method for treating pancreatic cancer in a subject, comprising administering to the subject in need thereof a therapeutically effective amount of a pharmaceutical formulation, wherein the pharmaceutical formulation comprises (Z)-butylidenephthalide and is substantially free of (E)-butylidenephthalide. Preferably, in the pharmaceutical formulation, (Z)-butylidenephthalide is included in a biocompatible polymer matrix so that the pharmaceutical formulation is used in a controlled release dosage form.

The detailed technology and the preferred embodiments implemented for the present invention will be described in the following paragraphs for people skilled in the field to appreciate the features of the claimed invention.

BRIEF DESCRIPTION OF THE DRAWINGS

The patent application contains at least one drawing executed in color. Copies of this patent document with color drawing(s) will be provided by the Office upon request and payment of the necessary fee.

DETAILED DESCRIPTION OF THE INVENTION

Figure 1A:
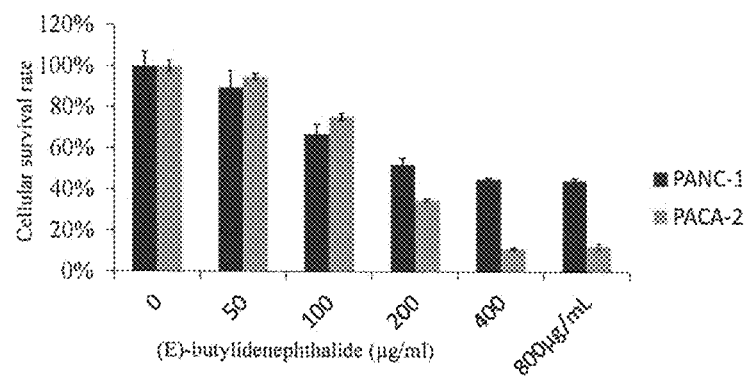
FIG. 1A is a bar diagram showing the effect of (E)-butylidenephthalide on the cell survival rate of a pancreatic cancer cell line.

The following will describe some embodiments of the present invention in detail. However, without departing from the spirit of the present invention, the present invention may be embodied in various embodiments and should not be limited to the embodiments described in the specification. In addition, unless otherwise state herein, the expressions "a," "the," or the like recited in the specification of the present invention (especially in the claims) should include both the singular and plural forms. Furthermore, the term "treat" or "treating" used in this specification refers to administering to a subject in need thereof a therapeutically effective amount of a pharmaceutical formulation, wherein the subject has a tumor or tumor signs, suffers from diseases or symptoms derived from tumor, or is susceptible to cancer, to achieve the effects of curing, mitigating, alleviating, treating or improving the tumor, tumor signs, diseases or symptoms derived from tumor, or the susceptibility to cancer. The term "effective amount" used in this specification refers to the amount of the compound that can at least partially alleviate the condition that is being treated in a suspected subject when being administered to the subject. The term "subject" used in this specification refers to a mammalian, including human and non-human animals. The term "mg/kg-body weight" used in this specification refers to the dosage (mg) required per kg-body weight. The term "controlled release dosage form" used in this specification refers to a dosage form which can slowly and continuously release the active component contained therein, after being administered to a subject.

Butylidenephthalide (BP) is a compound that is extractable from *Angelica sinensis*. The inventors of the present invention found that as compared to (E)-butylidenephthalide, (Z)-butylidenephthalide (i.e., the following compound (I)) is significantly effective in inhibiting the growth of pancreatic cancer cells and thus, can be used to treat pancreatic cancer:

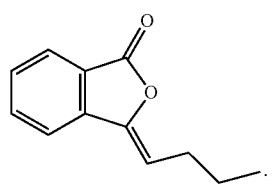

(I)

Therefore, the present invention provides a pharmaceutical formulation, comprising (Z)-butylidenephthalide, and is substantially free of (E)-butylidenephthalide. (Z)-butylidenephthalide is commercially available (for example, could be purchased from ECHO CHEMICAL CO., LTD, TW), and can be extracted from natural materials or separated from a chloroform extract of *Angelica sinensis*. (Z)-butylidenephthalide provided by extraction and separation can be further purified by techniques such as flash column chromatography, high performance liquid chromatography, or crystallization method prior to being used.

Optionally, the pharmaceutical formulation of the present invention may comprise a biocompatible polymer matrix, wherein (Z)-butylidenephthalide is included in the polymer matrix such that the pharmaceutical formulation can be used in a controlled release dosage form to provide a prolonged effect on treating pancreatic cancer. The biocompatible polymer matrix suitable for the present invention is generally hydrophobic and has an appropriate degradability. Preferably, the biocompatible polymer matrix is selected from the group consisting of poly(lactic-co-glycolic acid), chitosan, collagen, a hydrogel, a polyanhydride, and combinations thereof. When used in a controlled release dosage form, the pharmaceutical formulation of the present invention can slowly and continuously release (Z)-butylidenephthalide to tissue(s) adjacent to the administration site of a subject over a long period of time (e.g., in 20, 30, 35, 40, 50, 60 days) to achieve the effects of a continuous treatment of pancreatic cancer.

In one embodiment of the present invention, (Z)-butylidenephthalide was included in a polyanhydride to allow for the controlled release dosage form. Preferably, the polyanhydride is a copolymer of the following monomer (A) and monomer (B):

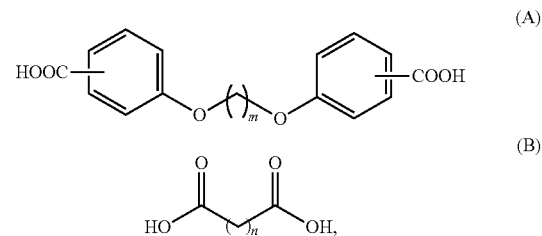

wherein m is an integer ranging from 1 to 10, and n is an integer ranging from 0 to 20. Preferably, m is an integer ranging from 2 to 8 and n is an integer ranging from 3 to 10. In addition, it is preferred that the two carboxyl groups on the benzene rings of monomer (A) are simultaneously in the ortho position, meta position or para position, and more preferably, in the para position.

Monomer (A) can be such as, but is not limited to, one or more of the following: bis(p-carboxy-phenoxy) ethane, bis(o-carboxy-phenoxy) ethane, bis(m-carboxy-phenoxy) ethane, bis(p-carboxy-phenoxy) propane, bis(o-carboxy-phenoxy) propane, bis(m-carboxy-phenoxy) propane, bis(p-carboxy-phenoxy) butane, bis(o-carboxy-phenoxy) butane, bis(m-carboxy-phenoxy) butane, bis(p-carboxy-phenoxy) pentane, bis(o-carboxy-phenoxy) pentane, bis(m-carboxy-phenoxy) pentane, bis(p-carboxy-phenoxy) hexane, bis(o-carboxy-phenoxy) hexane, Bis(m-carboxy-phenoxy) hexane, bis(p-carboxy-phenoxy) heptane, bis(o-carboxy-phenoxy) heptane, bis(m-carboxy-phenoxy) heptane, bis(p-carboxy-phenoxy) octane, bis(o-carboxy-phenoxy) octane, and bis(m-carboxy-phenoxy) octane. Preferably, monomer (A) is one or more of the following: bis(p-carboxy-phenoxy) ethane, bis(p-carboxy-phenoxy) propane, bis(p-carboxy-phenoxy) butane, bis(p-carboxy-phenoxy) pentane, bis(p-carboxy-phenoxy) hexane, bis(p-carboxy-phenoxy) heptane, and bis(p-carboxy-phenoxy) octane.

The monomer (B) suitable for the present invention can be such as, but is not limited to, one or more of the following: malonic acid, succinic acid, glutaric acid, adipic acid, pimelic acid, suberic acid, azelaic acid, and sebacic acid. In one embodiment of the present invention, sebacic acid was used as monomer (B).

Preferably, in the polyanhydride being used as the biocompatible polymer matrix, the molar ratio of monomer (A) to monomer (B) is from about 1:2 to about 1:10, and more preferably from about 1:3 to about 1:6. Furthermore, it is preferred that the biocompatible polymer matrix is a block copolymer of monomer (A) and monomer (B). In one embodiment of the present invention, the biocompatible polymer matrix is a polyanhydride, which is a block copolymer provided by bis(p-carboxyphenoxy)propane and sebacic acid at a molar ratio of 1:4.

The biocompatible polymer matrix that is suitable for the pharmaceutical formulation of the present invention is commercially available or can be prepared by synthesis methods known in the art. For example, for preparing a polyanhydride from bis(p-carboxyphenoxy) propane and sebacic acid, bis(p-carboxyphenoxy)propane and sebacic acid are separately refluxed in acetic anhydride to obtained sebacic acid prepolymer and bis(p-carboxyphenoxy) propane prepolymer, respectively. Then, the two prepolymers are copolymerized by a melt polycondensation method to provide a block copolymer (referred to as "p (CPP-SA) copolymer"), which is a polyanhydride. The steps of the melt polycondensation method can be seen in Domb et al., Journal of Polymer science, 1987, 25: 3373-3386, which is entirely incorporated herein by reference.

In the pharmaceutical formulation of the present invention, the ratio of (Z)-butylidenephthalide in the formulation could be adjusted depending on practical requirements. For example, the concentration of (Z)-butylidenephthalide in the pharmaceutical formulation can range from about 1% by weight to about 40% by weight, and preferably about 2% by weight to about 30% by weight.

According to the present invention, the pharmaceutical formulation can be used to provide a medicament in any suitable administration form to be applied in any suitable way. For example, the pharmaceutical formulation can be manufactured into a form of such as a wafer, powder, a membrane, a flake, a rod, a microparticle, a nanoparticle, a paste, or a gel, but is not limited thereby. In addition, the pharmaceutical formulation can be manufactured into a form that is suitable for oral administration, subcutaneous implantation, interstitial implant, intra-pancreas implantation, nasal administration, or intravenous injection, etc.

Using the manufacturing of a medicament in a dosage from suitable for oral administration as an example, the pharmaceutical formulation may comprise a pharmaceutically acceptable carrier which has no adverse effect on the desired activity of the active component, such as a solvent, oily solvent, diluent, stabilizer, absorption delaying agent, disintegrant, emulsifier, antioxidant, binder, lubricants, and moisture absorbent. The pharmaceutical formulation can be prepared into a medicament in an oral administration form by any suitable methods. For example, the pharmaceutical formulation can be used to manufacture a medicament as a tablet, a capsule, a granule, powder, a fluid extract, a solution, syrup, a suspension, an emulsion, a tincture, etc.

As for the manufacture of a medicament in a dosage from suitable for subcutaneous injection or intravenous injection, the pharmaceutical formulation may comprise one or more components such as an isotonic solution, a saline buffer solution (e.g., a phosphate buffer or a citric acid salt buffer), a solubilizer, an emulsifier, and other carriers to manufacture the formulation as an intravenous injection, an emulsion intravenous injection, a powder injection, a suspension injection, or a powder-suspension injection, etc.

Depending on the form and purpose, the pharmaceutical formulation of the present invention may comprise one or more pharmaceutically acceptable carriers. In addition to the carrier(s), the pharmaceutical formulation may optionally comprise other additives, such as a flavoring agent, a toner, a coloring agent, etc. to enhance the taste and visual appeal of the resultant formulation. To improve the storability of the medicament thus provided, the formulation may also comprise a suitable amount of a preservative, a conservative, an antiseptic, an anti-fungus reagent, etc. Optionally, the pharmaceutical formulation of the present invention may comprise one or more other active components, such as an antioxidant (e.g., vitamin E), chemotherapy drugs, immune modulators, etc., to further enhance the efficacy of the medicament thus provided or to increase the application flexibility and adaptability of the medicament, as long as the other active components have no adverse effect on (Z)-butylidenephthalide.

In the case that the pharmaceutical formulation of the present invention comprises a biocompatible polymer matrix, the pharmaceutical formulation is preferably manufactured as a medicament in a dosage form suitable for subcutaneous implantation, interstitial implant, and intra-pancreas implantation (such as a wafer) so that the pharmaceutical formulation can slowly release (Z)-butylidenephthalide to the tissue adjacent to the administration site of a subject after being administrated to the subject to achieve a therapeutic efficacy at a locally stable high dose. As a result, the pharmaceutical formulation can be directly implanted around the tumor (e.g., pancreatic tumor) and release (Z)-butylidenephthalide to the tissue adjacent to the administration site over a certain period of time (e.g., in 20, 30, 35, 40, 50, 60 days) to slowly and continuously release (Z)-butylidenephthalide, and thereby, achieve the effects of a prolonged treatment of pancreatic cancer and/or reducing the recurrence of pancreatic cancer.

Using the manufacture of a medicament in a dosage form suitable for subcutaneous implantation, interstitial implant, and intra-pancreas implantation as an example, the pharmaceutical formulation can comprise a pharmaceutically acceptable carrier which has no adverse influence on the activity of the active component comprised therein, such as an excipient, stabilizer, and moisture absorbent, etc., to prepare a medicament in a form for subcutaneous implantation, interstitial implant, and intra-pancreas implantation, such as a wafer, a tablet, a capsule, a granule. In one embodiment of the present invention, (Z)-butylidenephthalide was mixed with p(CPP-SA) copolymer to provide a mixture, and then the mixture was dissolved in dichloromethane and dried to form a powder. Then, the dried powder was filled in a mold and compressed under slight pressure to form a medicament as a wafer for subcutaneous implantation, interstitial implant, and intra-pancreas implantation. After the pancreatic tumor in a patient of pancreatic cancer was excised, the wafer (i.e., a pharmaceutical formulation comprising (Z)-butylidenephthalide and p(CPP- SA) copolymer) was implanted into the diseased region in the patient, to more thoroughly treat pancreatic cancer and/or reduce the recurrence of pancreatic cancer. The aforementioned method for preparing the wafer was further illustrated in the appended Examples and Walter et al., Cancer Res. 1994, 54(8): 2207-12, which is entirely incorporated herein by reference.

Depending on the requirements of the subject, the pharmaceutical formulation of the present invention or the medicament manufactured by using the pharmaceutical formulation can be applied with various administration frequencies, such as once a day, several times a day, or once every few days, etc. For example, when being administered to a human subject for treating pancreatic cancer, the pharmaceutical formulation is administered at an amount ranging from about 10 mg to about 1000 mg as (Z)-butylidenephthalide/kg-body weight per day, and preferably about 50 mg to about 500 mg as (Z)-butylidenephthalide/kg-body weight per day. However, for patients with acute conditions, the dosage can be increased to several times or several tens of times, depending on the practical requirements.

The present invention also provides a method for treating pancreatic cancer comprising administering to a subject in need thereof a therapeutically effective amount of a pharmaceutical formulation, wherein the pharmaceutical formulation comprises (Z)-butylidenephthalide and is substantially free of (E)-butylidenephthalide. Preferably, the pharmaceutical formulation further comprises a biocompatible polymer matrix, and (Z)-butylidenephthalide is included in the biocompatible polymer matrix. The components of the pharmaceutical formulation and its properties, and the efficacy and dosage of (Z)-butylidenephthalide are all as described above.

The present invention will be further illustrated in details with specific examples as follows. However, the following examples are provided only for illustrating the present invention, and the scope of the present invention is not limited thereby.

EXAMPLE

[Example 1] Killing Effects of (Z)-Butylidenephthalide on Different Pancreatic Cancer Cell Lines MTT (3-[4,5-dimethylthiahiazo-2-yl]-2,4-dipheny-tetrazolium bromide) was used to determine if the cell survival rate of different pancreatic cancer cell lines will be influenced when being treated with (Z)-butylidenephthalide. Human pancreatic cancer cell lines (3×103 cells/well), PANC-1 and PACA-2, were cultured in a 96-well microculture plate over night. Different concentrations of (Z)-butylidenephthalide (0 μg/ml, 10 μg/ml, 25 μg/ml, 50 μg/ml, 75 μg/ml, or 100 μg/ml) or (E)-butylidenephthalide (0 μg/ml, 50 μg/ml, 100 μg/ml, 200 μg/ml, 400 μg/ml, or 800 μg/ml), or 50 μM gemcitabine (a traditional medicine for treating pancreatic cancer, as a control group) were added into each well of the 96-well micro-culture plate along the inner wall, and cultured for 24 hours. The medium was removed, and then a medium containing 500 μg/ml MTT (200 μl) was added and cultured for 4 hours. The medium was removed, and then 200 μl of DMSO was added into the plate. The absorbance of the sample in each well was measured by a spectrophotometer at 570 nm wavelength. The data was calculated to determine the survival rate and IC50 (concentration of 50% inhibition) of each pancreatic cancer cell line treated with (Z)-butylidenephthalide and (E)-butylidenephthalide. The results are shown in FIG. 1A ((E)-butylidenephthalide) and FIG. 1B ((Z)-butylidenephthalide).

Figure 1B:
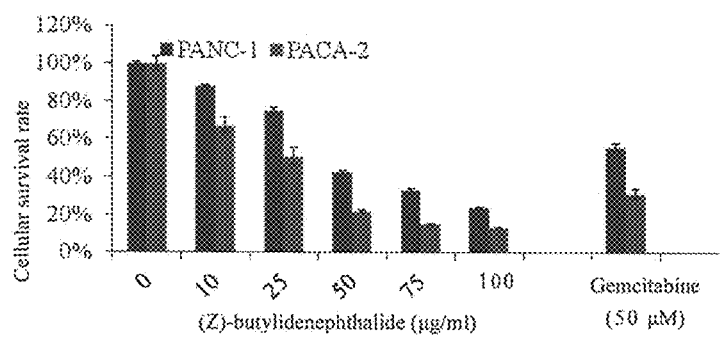
FIG. 1B is a bar diagram showing the effect of (Z)-butylidenephthalide on the cell survival rate of a pancreatic cancer cell line.

As shown in FIGS. 1A and 1B, the IC50 of (E)-butylidenephthalide was about 257.1 μg/ml (about 1367 μM) for PANC-1, and about 162.5 μg/ml (about 864.5 μM) for PACA-2. The IC50 of (Z)-butylidenephthalide for was about 45 μg/ml (about 234 μM) for PANC-1, and about 25 μg/ml (about 133 μM) for PACA-2. These experimental data show that the IC50 of (Z)-butylidenephthalide for the pancreatic cancer cell lines was far smaller than that of (E)-butylidenephthalide.

[Example 2] Preparation of a Controlled Release Dosage Form Containing Z-Butylidenephthalide (1) Preparation of SA Prepolymer Sebacic acid (SA) was recrystallized twice by ethanol. 2.7 g sebacic acid monomer was added into 60 ml of acetic anhydride, and refluxed under vacuum ($10^{-4}$ torr) at 135° C. to 140° C. for 30 minutes. Then, the unreacted acetic anhydride was removed to obtain an SA prepolymer. The SA prepolymer was dried under vacuum at 60° C., and then dissolved in dry toluene. The obtained solution was mixed with a mixture of absolute ether and petroleum ether (1:1 vol/vol) in a ratio of 1:10 by volume and allowed to stand overnight to precipitate the SA prepolymer (10:1 vol/vol). Then, the absolute ether and petroleum ether were removed and the obtained SA prepolymer was dried under vacuum.

(2) Preparation of CPP Prepolymer 3 g bis(p-carboxyphenoxy)propane (CPP) and 50 ml of acetic anhydride were mixed, and refluxed under vacuum ($10^{-4}$ torr) at 150° C. for 30 minutes and cooled. The mixture was then filtrated. The filtrate was concentrated by removing the unreacted acetic anhydride. Then, crystallization was performed at 0° C. to obtain the CPP prepolymer. The unreacted acetic anhydride was removed to obtain a CPP prepolymer. The CPP prepolymer was washed with ether and dried under vacuum. Then, dimethylformamide and absolute ether (volume ratio of dimethylformamide and absolute ether is 1:9) were sequentially added to the CPP prepolymer. After 12 hours the dimethylformamide and ether were removed. The obtained CPP crystal prepolymer was dried under vacuum.

(3) Preparation of p(CPP-SA) Copolymer

Figure 2:
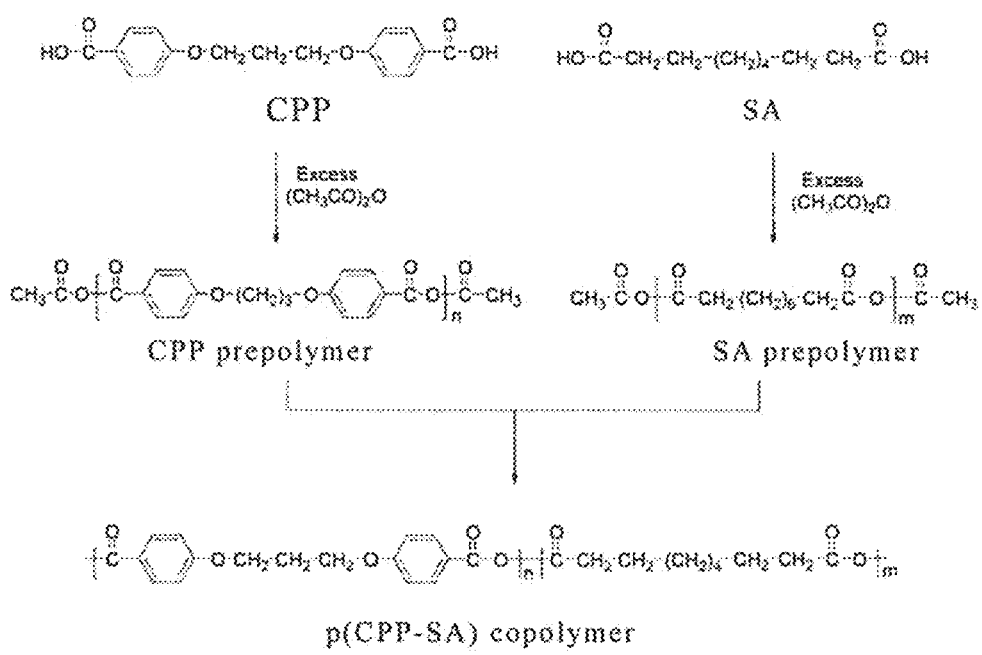
FIG. 2 is a flow chart of preparing a p(CPP-SA) copolymer.

CPP prepolymer and SA prepolymer (with a molar ratio of 20:80) were filled into a glass tube (2×20 cm), heated at 180° C. in an oil bath for 1 minute, and then the pressure was reduced to $10^{-4}$ mm Hg. In the polymerization process, the vacuum was eliminated every 15 minutes. The tube was cleaned with dichloromethane and then petroleum ether was added to precipitate the CPP prepolymer and SA prepolymer copolymer (referred to as "p(CPP-SA) copolymer"). Then, the p(CPP-SA) copolymer was washed with anhydrous ether. The aforementioned preparation process was as shown in FIG. 2.

The characteristics of the obtained p(CPP-SA) copolymer was analyzed by infrared spectroscopy (IR) and nuclear magnetic resonance spectroscopy (1H NMR) (data not shown). The experimental results show that there is a signal of anhydride bond that can be observed at 1812.76 $cm^{-1}$. In the 1H NMR spectrum of the p(CPP-SA) copolymer, the characteristic signal of the aromatic portion of CPP can be observed at 6.9 ppm to 8.2 ppm, and the characteristic signal of the methylene portion of SA can be observed at 1.3 ppm.

In addition, according to the peak intensity of CPP and SA in the 1H NMR spectrum, the molar ratio of CPP and SA in the p(CPP-SA) copolymer was determined as about 1:4 to about 1:5.

Figure 3:
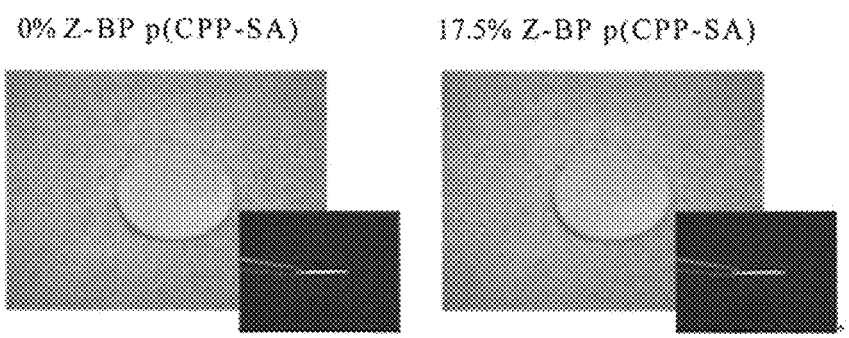
FIG. 3 shows pictures of two p(CPP-SA)-Z-BP wafers, wherein the concentration of Z-BP in the left one is 0% and that in the right one is 17.5%.

(4) Preparation of p(CPP-SA)-Z-BP Pharmaceutical Formulation (Z)-butylidenephthalide (ECHO CHEMICAL CO., LTD, TW) was mixed with the p(CPP-SA) copolymer by a weight ratio of about 0 w %, 17.5 w %, 25 w %. The mixture was dissolved in methylene chloride at a concentration of 10% (weight/volume). The solution was dried under vacuum for 72 hours to obtain a dried powder. The dried powder was compressed under a slight pressure (Carver Press) of 200 psi by using a stainless steel mold (with an internal diameter of 13 mm) to form a wafer (100 mg/wafer). The wafer comprises the pharmaceutical formulation comprising (Z)-butylidenephthalide and p(CPP-SA) copolymer, herein after referred to as "p(CPP-SA)-Z-BP. The appearance of the wafer is as shown in FIG. 3.

[Example 3] Drug Release Kinetics Test of p(CPP-SA)-Z-BP Pharmaceutical Formulation The p(CPP-SA)-Z-BP wafer (comprising 17.5% Z-BP or 25% Z-BP) prepared in Example 2 was added into a scintillation vial containing 1.0 ml of phosphate-buffered saline (0.1 mM, pH 7.4) and 1.0 ml of n-octanol, and incubated at 37° C. The solution was replaced by a fresh buffer solution at various time points, and the absorbance of the solution was measured at 310 nm using a spectrophotometer to measure the concentration of (Z)-butylidenephthalide in the buffer. The aforementioned method was described by Weingart et al., Int. J. Cancer. 1995, 62(5): 605-9, which is entirely incorporated herein by reference.

Figure 4:
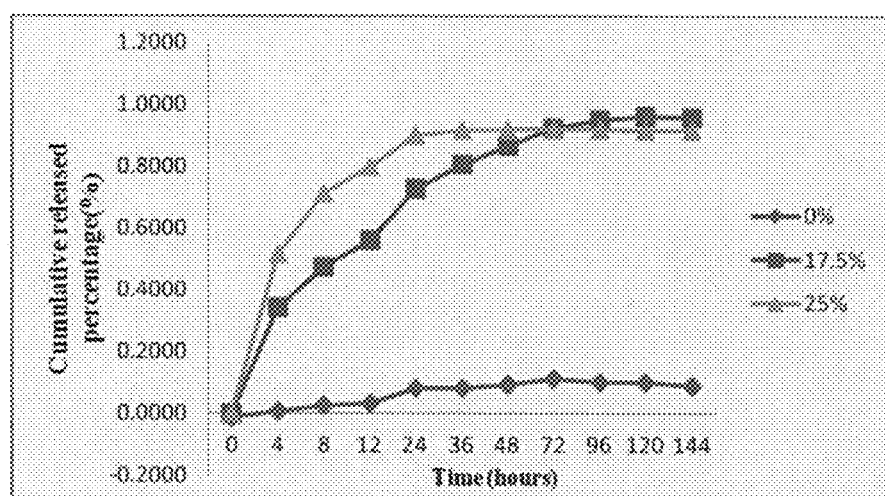
FIG. 4 is a curve diagram of the absorbance showing the continuous and slow release of p(CPP-SA)-Z-BP wafers from 0 to 25 days.

As shown in FIG. 4, the p(CPP-SA)-Z-BP wafer can continuously and slowly release the active component contained therein from 0 to 144 hours. These data show that the p(CPP-SA)-Z-BP can be used as a controlled release dosage form containing (Z)-butylidenephthalide. Therefore, when a p(CPP-SA)-Z-BP wafer was implanted into a subject, Z-butylidenephthalide can slowly and continuously be released to the surrounding pancreatic tissue, and thus can achieve a continued therapeutic effect.

[Example 4] Cellular Experiment: Cytotoxic Effect of p(CPP-SA)-Z-BP Pharmaceutical Formulation Human pancreatic cancer cell lines, PACA-2, was cultured with p(CPP-SA)-Z-BP comprising 0 w % (as a control group), 17.5 w %, or 25 w % (Z)-butylidenephthalide, respectively, for 24 hours, and then the tumor cell morphology and cellular survival rate were observed.

Figure 5A:
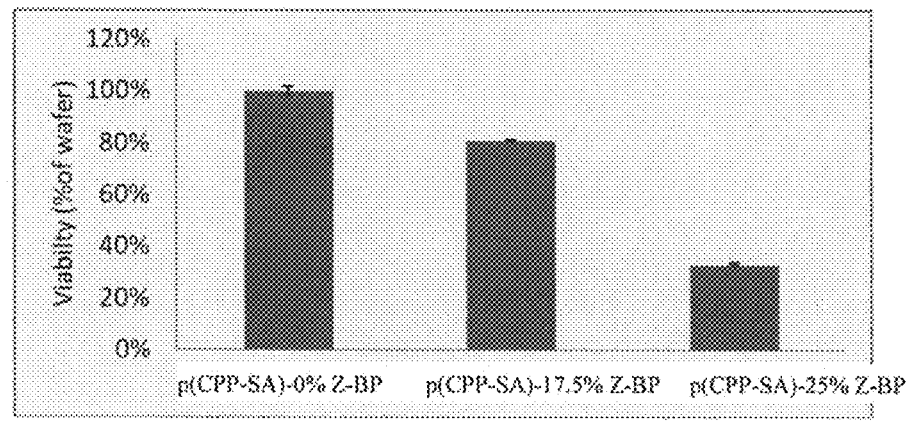
FIG. 5A is a bar diagram showing the effect of p(CPP-SA)-Z-BP on reducing the survival rate of PACA-2 cells.
Figure 5B:
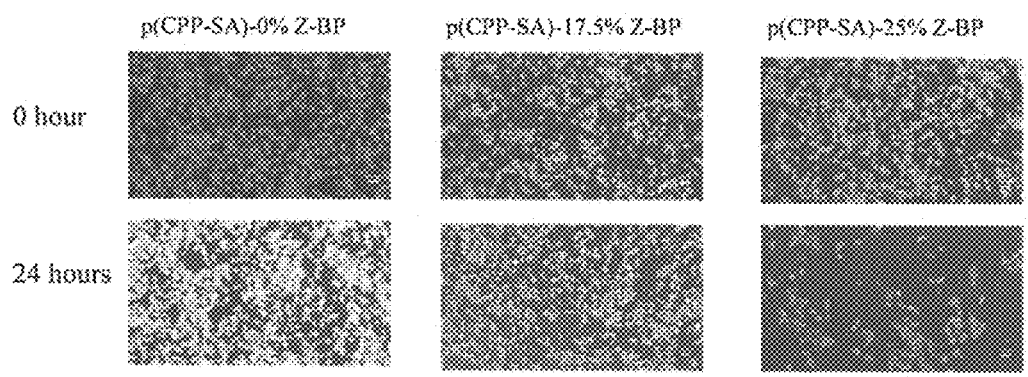
FIG. 5B shows pictures illustrating the effect of p(CPP-SA)-Z-BP on inducing the apoptosis of PACA-2 cells.

As shown in FIG. 5A, as compared to the control group (i.e., p(CPP-SA) without (Z)-butylidenephthalide), p(CPP-SA)-Z-BP comprising 17.5 w %, or 25 w % (Z)-butylidenephthalide can effectively reduce the survival rate of PACA-2 cell line. As shown in FIG. 5B, the treatment of p(CPP-SA)-Z-BP comprising 17.5 w %, or 25 w % (Z)-butylidenephthalide caused the apoptosis of PACA-2 cell line. The aforesaid experimental data show that the p(CPP-SA)-Z-BP pharmaceutical formulation of the present invention can effectively inhibit the growth of pancreatic cancer cell.

[Example 5] Cellular Experiment: Apoptosis Induced by Z-BP (1) Analysis of the Expression Level of mRNA It has been known that the up-regulated expression of orphan receptor-1 (NOR-1), Nurr1, Nur77 are related to apoptosis. In this experiment, pancreatic cancer cell lines, PANC-1 and PACA-2, were treated with 100 μg/ml Z-BP for 0, 1, 3, 6, or 24 hours, and then, analyzed by reverse transcriptase-polymerase chain reaction (RT-PCR) (FIG. 6A) to analyze the effects of Z-BP on the gene expression levels of NOR-1, Nurr1, and Nur77 in the pancreatic cancer cell line. In addition, pancreatic cancer cell lines, PANC-1 and PACA-2, were treated with different concentrations of Z-BP for 3 hours, and then, analyzed by RT-PCR (FIG. 6B). The Glyceraldehyde 3-phosphate dehydrogenase (GAPDH) was used as the control group.

Figure 6A:
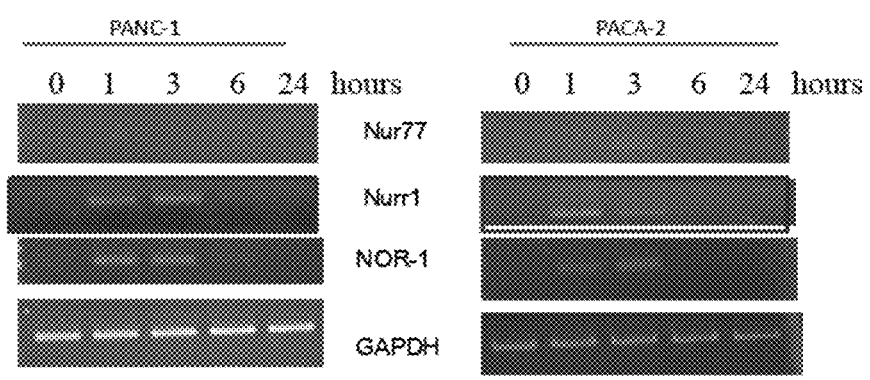
FIG. 6A shows electrophoregrams illustrating the increase of apoptosis-related genes expression levels in pancreatic cancer cell lines at different times after the pancreatic cancer cell lines were treated with Z-BP.
Figure 6B:
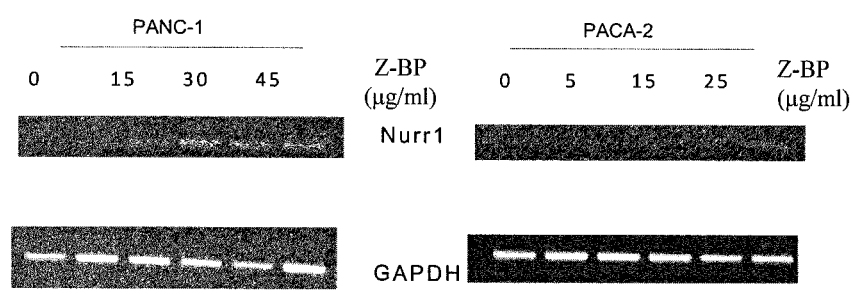
FIG. 6B shows electrophoregrams illustrating the increase of apoptosis-related genes expression levels in the pancreatic cancer cell lines that were treated with Z-BP at different concentrations.

As shown in FIG. 6A, after the pancreatic cancer cell lines, PANC-1 and PACA-2, were treated with Z-BP for 1 to 3 hours, the mRNA expression levels of NOR-1 and Nurr1 in the pancreatic cancer cell line were increased. As shown in FIG. 6B, after the pancreatic cancer cell lines, PANC-1 and PACA-2, were treated with different concentrations of Z-BP for 3 hours, the mRNA expression levels of Nurr1 in the pancreatic cancer cell line were increased. These results show that the up-regulated expression of Nurr1 in may cause by the apoptosis induced by Z-BP.

(2) Micro RNA Interference Test

Figure 7A:
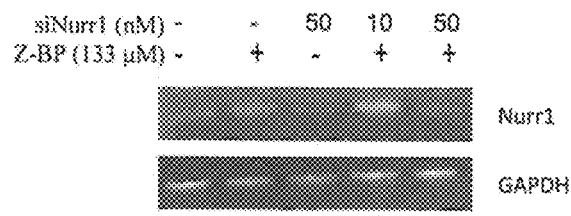
FIG. 7A shows electrophoregrams illustrating the treatment of PACA-2 with Nurr1 micro RNA to inhibit the Z-BP induced-expression level of Nurr1 gene.

The RNA expression of Nurr1 in the human pancreatic cancer cell line, PACA-2, was inhibited by Micro RNA interference technology. The cells were treated with 133 μM Z-BP. Then, the cells were analyzed by RT-PCR to detect the changes in the expression of Nurr1 RNA in the cells. As the results shown in FIG. 7A, when PACA-2 cells were treated with 50 nM Nurr1 micro RNA, about 50% of the Nurr1 induced by Z-BP was inhibited. These results show that Z-BP treatment indeed can increase the expression of Nurr1.

Figure 7B:
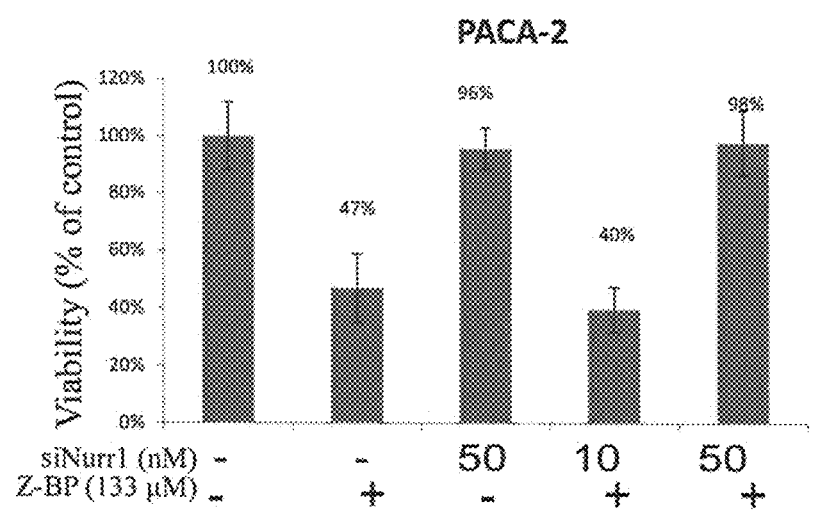
FIG. 7B is a bar diagram illustrating the treatment of PACA-2 with Nurr1 micro RNA to restore the cell survival rate deceased by Z-BP.

In addition, the human pancreatic cancer cell line, PACA-2, was treated with 10 nM or 50 nM of Nurr1 micro RNA, and then treated with 133 μM Z-BP. Then, the cellular survival rate was observed using the same method as described in Example 4. As shown in FIG. 7B, after PACA-2 cells were treated with 50 nM of Nurr1 micro RNA, the cellular survival rate inhibited by Z-BP can be restored. These results shown that Z-BP treatment will reduce the cellular survival rate of PACA-2 cells.

(3) Western Blotting Test

Figure 8A:
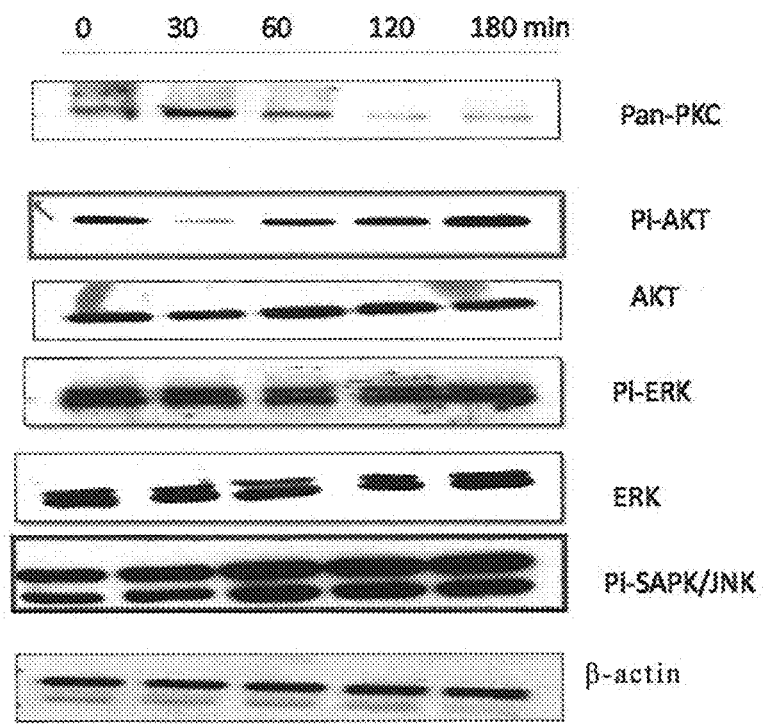
FIG. 8A shows electrophoregrams illustrating the effect of Z-BP on increasing the expression levels of Nur77 gene pathway-related proteins in pancreatic cancer cells.

Human pancreatic cancer cell line, PACA-2, was treated with Z-BP for 0, 30, 60, 120, or 180 minutes, and then the expression levels of the Nur77 gene involved pathway-related proteins were analyzed by Western blotting, including Pan-PKC, AKT, ERK, and JNK (FIG. 8A). In addition, the expression levels of apoptosis-related proteins were also analyzed, including poly(ADP-ribose) polymerase (PARP), cleaved poly(ADP-ribose) polymerase (cPARP), caspase-3 (FIG. 8B). β-actin was used as the control group.

Figure 8B:
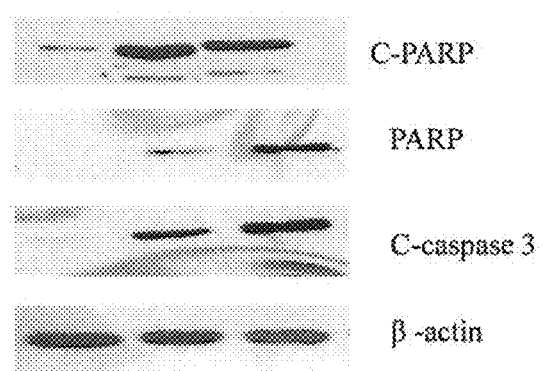
FIG. 8B shows electrophoregrams illustrating the effect of Z-BP on increasing the expression levels of apoptosis pathway-related proteins in pancreatic cancer cells.

As shown in FIG. 8A, after the PACA-2 cells were treated with Z-BP for 180 minutes, the expression levels of phospho-JNK (Pi-SAPK/JNK) and phospho-AKT (Pi-AKT) in the PACA-2 cells were increased, showing that Z-BP treatment can increase the expression levels of the Nur77 gene pathway-related proteins. As shown in FIG. 8B, after the PACA-2 cells were treated with Z-BP for 24 hours or 48 hours, the expression levels of caspase-3, PARP and cPARP in the PACA-2 cells were increased, showing that Z-BP treatment can increase the expression levels of the apoptosis-related proteins.

[Example 6] Animal Experiments:
p(CPP-SA)-Z-BP Reduce the Size of Pancreatic Tumors in Mice Nude mice (6 mice/group) were treated with subcutaneous back implant including PACA-2 cells (1×106 cells). Then, p(CPP-SA)-Z-BP comprising 0% (control group), 17.5%, or 25% Z-BP were implanted into the mice though the region implanted with the PACA-2 cells. Then, the size of the tumor in each mice was measured by a calibrator, and the body weight of each mice was measured. The tumor volume was calculated by the formula of length×height×width×0.5236 (L×H×W×0.5236) (cubic millimeters). The results are shown in FIGS. 9 and 10.

Figure 9:
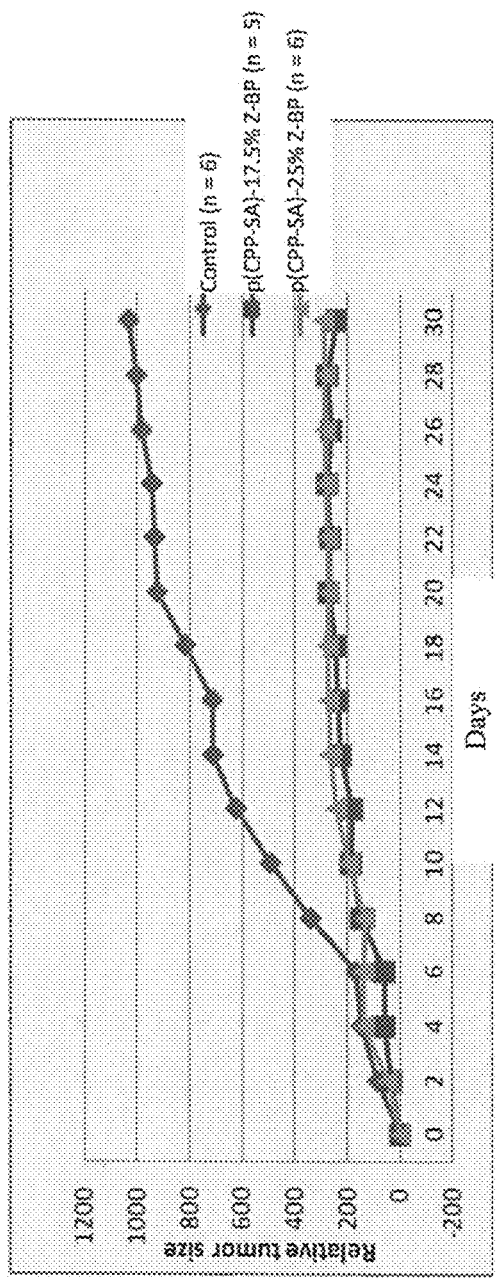
FIG. 9 is a curve diagram showing the size of pancreatic tumor in the mice that were subcutaneously implanted with p(CPP-SA)-Z-BP at different Z-BP concentrations.
Figure 10:
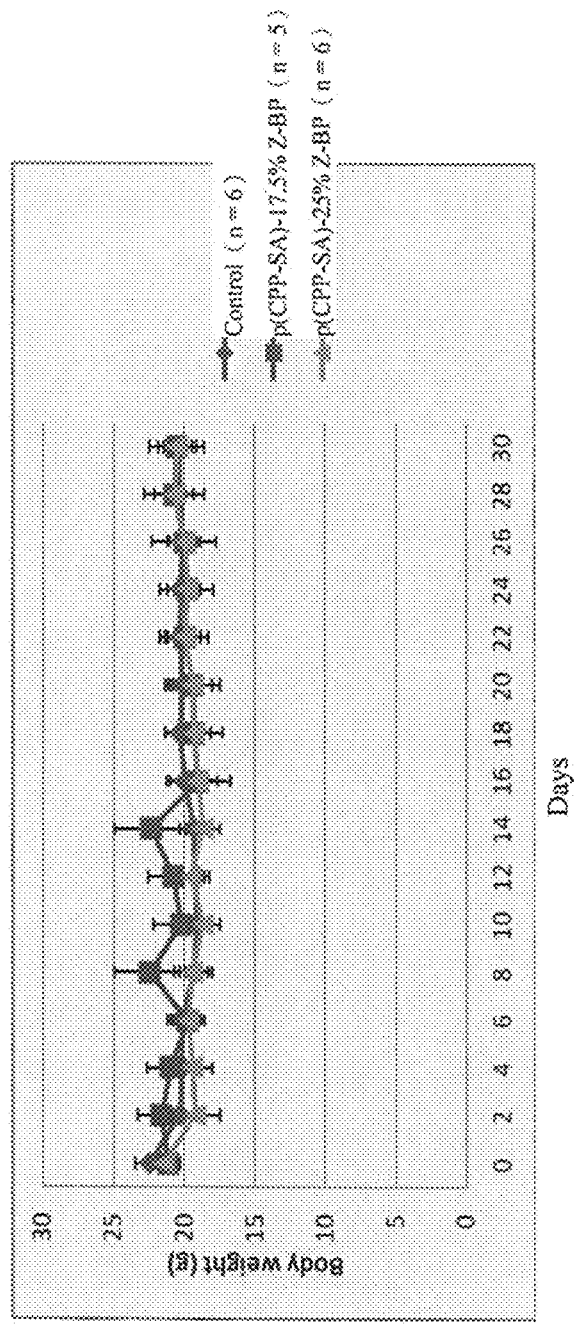
FIG. 10 is a curve diagram showing the body weight of the mice that were subcutaneously implanted with p(CPP-SA)-Z-BP at different Z-BP concentrations.

As shown in FIG. 9, the relative size of the pancreatic tumors in the mice in the control group (the mice treated with p(CPP-SA)-Z-BP without Z-BP) was quickly expanded to more than 1000 after 30 days from the beginning of the experiment; while the relative size of the pancreatic tumors in the mice in the experiment group (the mice treated with p(CPP-SA)-Z-BP comprising 17.5% or 25% Z-BP) was about 200. As shown in FIG. 10, there are no significant change in the body weight of the mice in each group. These experimental results show that p(CPP-SA)-Z-BP treatment can effectively inhibit the growth of the pancreatic tumor in mice.

The above experimental results show that the pharmaceutical formulation comprising (Z)-butylidenephthalide of the present invention can effectively inhibit the growth of the pancreatic cancer cells, and thus, can be used to treat pancreatic cancer. In addition, the pharmaceutical formulation of the present invention can further comprise a hydrophobic biocompatible polymer to form a controlled release dosage form, and thereby, provide a slow and continuous treatment effect on pancreatic cancer.

The above examples are used to illustrate the principle and efficacy of the present invention but not used to limit to the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

What is claimed is:

1. A method for treating pancreatic cancer comprising administering to a subject in need thereof a therapeutically effective amount of a pharmaceutical formulation, wherein the pharmaceutical formulation comprises (Z)-butylidenephthalide and is substantially free of (E)-butylidenephthalide.

2. The method of claim 1, wherein the pharmaceutical formulation further comprises a biocompatible polymer matrix, and (Z)-butylidenephthalide is included in the matrix.

3. The method of claim 2, wherein the biocompatible polymer matrix is selected from the group consisting of poly(lactic-co-glycolic acid), chitosan, collagen, a hydrogel, a polyanhydride, and combinations thereof.

4. The method of claim 2, wherein the biocompatible polymer matrix is a polyanhydride.

5. The method of claim 4, wherein the polyanhydride is a copolymer of monomer (A) and monomer (B):

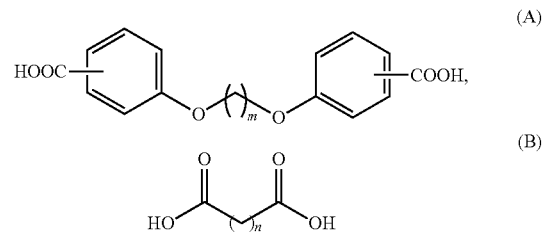

wherein,
m is an integer ranging from 1 to 10, and
n is an integer ranging from 0 to 20.

6. The method of claim 5, wherein m is an integer ranging from 2 to 8 and n is an integer ranging from 3 to 10.

7. The method of claim 5, wherein the polyanhydride is a block copolymer of monomer (A) and monomer (B).

8. The method of claim 6, wherein the monomer (A) is bis(p-carboxy-phenoxy)propane and monomer (B) is sebacic acid.

9. The method of claim 5, wherein the molar ratio of the monomer (A) and monomer (B) ranges from about 1:2 to about 1:10.

10. The method of claim 9, wherein the molar ratio of the monomer (A) and monomer (B) ranges from about 1:3 to about 1:6.

11. The method of claim 1, wherein the concentration of (Z)-butylidenephthalide in the pharmaceutical formulation is about 1% by weight to about 40% by weight.

12. The method of claim 11, wherein the concentration of (Z)-butylidenephthalide is about 2% by weight to about 30% by weight.

13. The method of claim 1, wherein the pharmaceutical formulation is provided as a wafer, powder, a membrane, a flake, a rod, a microparticle, and nanoparticle, a paste, or a gel.

14. The method of claim 13, wherein the pharmaceutical formulation is provided as a wafer.

15. The method of claim 1, wherein the pharmaceutical formulation is administered by at least one of subcutaneous implantation, interstitial implant, and intra-pancreas implantation.

16. The method of claim 1, wherein the pharmaceutical formulation is administered at an amount ranging from about 10 mg (as (Z)-butylidenephthalide)/kg-body weight to about 1,000 mg (as (Z)-butylidenephthalide)/kg-body weight per day.

17. The method of claim 16, wherein the pharmaceutical formulation is administered at an amount ranging from about 50 mg (as (Z)-butylidenephthalide)/kg-body weight to about 500 mg (as (Z)-butylidenephthalide)/kg-body weight per day.

18. The method of claim 8, wherein the molar ratio of the monomer (A) and monomer (B) is about 1:4.

* * * * *